United States Patent [19]

Nakajima et al.

[11] Patent Number: 4,877,511
[45] Date of Patent: Oct. 31, 1989

[54] OXYGEN CONCENTRATION-SENSING DEVICE

[75] Inventors: Toyohei Nakajima; Toshiyuki Mieno, both of Wako, Japan

[73] Assignee: Honda Giken Kogyo Kabushiki Kaisha, Tokyo, Japan

[21] Appl. No.: 290,955

[22] Filed: Dec. 28, 1988

[30] Foreign Application Priority Data

Dec. 28, 1987 [JP] Japan ................................. 62-332845

[51] Int. Cl.$^4$ ............................................. G01N 27/58
[52] U.S. Cl. ................................................. 204/406
[58] Field of Search .................. 204/406, 412, 425, 15

[56] References Cited

U.S. PATENT DOCUMENTS 4,615,787 10/1986 Yamada et al. ........................ 204/406
4,777,922 10/1988 Mieno et al. .......................... 123/479
4,787,966 11/1988 Nakajima et al. ..................... 204/406

*Primary Examiner*—G. L. Kaplan
*Attorney, Agent, or Firm*—Pollock, Vande Sande & Priddy

[57] ABSTRACT

An oxygen concentration-sensing device includes an oxygen concentration-sensing element formed by an oxygen-pumping element and a cell element, each composed of an oxygen ion-conductive electrolytic member and a pair of electrodes having the member interposed therebetween. The two elements define a gas diffusion-limiting zone therebetween. A current-to-voltage converter circuit has an input terminal connected to the junction between mutually connected ones of the electrodes. A first amplifier generates an output having a level variable in response to the difference between a potential at a conversion output terminal of the current-to-voltage converter circuit and a potential at the other electrode of the cell element, and applies the output to the other electrode of the oxygen-pumping element. A second amplifier has an input thereof connected to the above junction and generates an output proportional to current flowing in the oxygen-pumping element. The current-to-voltage converter circuit imparts a higher gain to the first amplifier when pumping current flowing in the oxygen-pumping element is in a high frequency range.

4 Claims, 2 Drawing Sheets

OXYGEN CONCENTRATION-SENSING DEVICE

BACKGROUND OF THE INVENTION

This invention relates to an oxygen concentration-sensing device of the type which generates an output proportional to the concentration of oxygen in a gaseous substance such as exhaust gases emitted from an internal combustion engine.

An air-fuel ratio control system for an internal combustion engine is known e.g. from Japanese Pat. Publication (Kokoku) No. 55-3533, which senses the concentration of oxygen in exhaust gases emitted from the engine by means of an oxygen concentration sensing device, and controls the air-fuel ratio of a mixture supplied to the engine to a desired value in a feedback manner responsive to the output from the oxygen sensor, to thereby purify the exhaust gases and improve the fuel consumption, etc.

The above-mentioned oxygen concentration-sensing device for use in an air-fuel ratio control system includes a type which generates an output proportional to the concentration of oxygen contained in the exhaust gases, i.e. the air-fuel ratio in the exhaust gases. An oxygen concentration-sensing device of this type is disclosed, e.g. in Japanese Provisional Pat. Publication (Kokai) No. 59-192955, which comprises an oxygen-pumping element and a cell element, each being composed of a plate-like member formed of a solid electrolytic material having oxygen ion-conductivity, and a couple of electrodes attached to opposite side surfaces of the plate-like member. A gas-staying chamber is partly defined by one of the electrodes of each of the oxygen-pumping element and the cell element. A gas to be examined is introduced into the gas-staying chamber through a gas-introducing slit. An air chamber into which the atmosphere is introduced is provided adjacent the cell element, with the other of the coupled electrodes of the cell element facing the interior of the air chamber.

According to this oxygen concentration-sensing device, in order to maintain the concentration of oxygen present within the gas-staying chamber at a predetermined value (e.g. 0), a voltage developed across the cell element is compared with a predetermined reference value, and pumping current is caused to flow between the two electrodes of the oxygen-pumping element in response to the result of the comparison. The value of the pumping current is outputted as an output proportional to the oxygen concentration in the gas to be examined.

In the above proportional output-type oxygen concentration-sensing device, as stated above, the concentration of oxygen within the gas-staying chamber is controlled in a feedback manner by varying the pumping current flowing in the oxygen-pumping element in response to the voltage developed across the cell element. There can occur phase rotation or phase delay in the feedback system, depending upon the frequency of variation of the pumping current value. If the loop gain of the feedback system is 1 or more at frequencies where the phase rotation exceeds 180 degrees, there can occur oscillation. Such oscillation can easily occur particularly when the pumping current is in a high frequency range, because the detection gain of an oxygen concentration-sensing element composed of the oxygen-pumping element and the cell element, i.e. the amount of change in the voltage developed across the cell element per unit amount of change in the pumping current is small in the high frequency range, as shown in FIG. 1.

SUMMARY OF THE INVENTION

It is therefore the object of the invention to provide an oxygen concentration-sensing device which is free from oscillation and is capable of accurately detecting the value of the pumping current.

To attain the above object, the present invention provides an oxygen concentration-sensing device including an oxygen concentration-sensing element formed by an oxygen-pumping element and a cell element, each composed of a member of a solid electrolytic material having oxygen ion-conductivity, and a pair of electrodes having the member interposed therebetween, one of the electrodes of the oxygen-pumping element and one of the electrodes of the cell element being connected to each other, the oxygen-pumping element and the cell element defining a gas diffusion-limiting zone therebetween, a current-to-voltage converter circuit having an input terminal connected to a junction between the connected ones of the electrodes, and a conversion output terminal, first amplifier means for generating an output having a level variable in response to a difference between a potential at the conversion output terminal of the current-to-voltage converter circuit and a potential at the other of the electrodes of the cell element, the first amplifier means applying the output thereof to the other of the electrodes of the oxygen-pumping element, and second amplifier means having an input thereof connected to the junction between the connected ones of the electrodes for generating an output proportional to current flowing in the oxygen-pumping element.

The oxygen concentration-sensing device according to the invention is characterized by an improvement wherein the current-to-voltage converter circuit includes gain-changing means for imparting a higher gain to the first amplifier means when the current flowing in the oxygen-pumping element is in a high frequency range.

The gain-changing means of the current-to-voltage converter circuit may comprise means for making the potential at the conversion output terminal closer or equal to a potential at the junction between the connected ones of the electrodes when the current flowing in the oxygen-pumping element is in the high frequency range.

In a preferred embodiment of the invention, the current-to-voltage converter circuit comprises a resistance connected between the junction between the connected ones of the electrodes and the conversion output terminal, a voltage-dividing circuit having a divided voltage output terminal and connected between an output terminal and an inverting input terminal of the first amplifier means, and a capacitive impedance element connected between the divided voltage output terminal of the voltage-dividing circuit and the conversion output terminal.

The above and other objects, features, and advantages of the invention will be more apparent from the ensuing detailed description taken in conjunction with the accompanying drawings.

DETAILED DESCRIPTION

The invention will now be described in detail with reference to the drawings showing an embodiment thereof.

Figure 1:
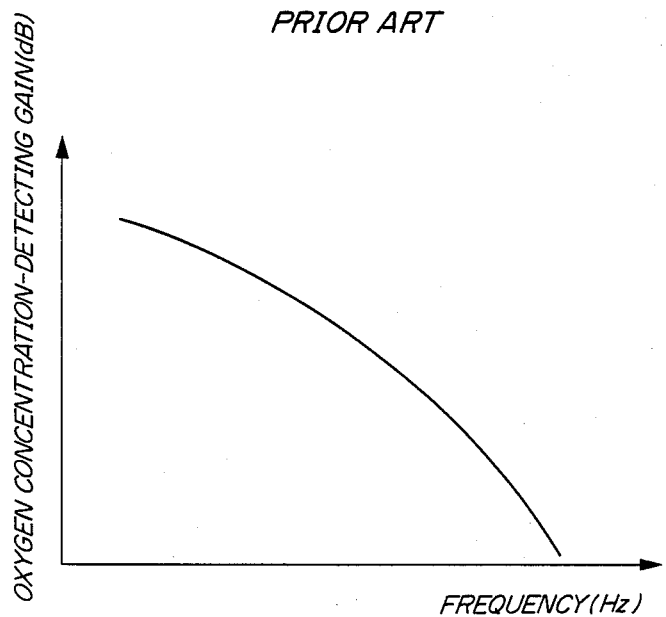
FIG. 1 is a graph showing oxygen concentration-detecting gain vs. frequency in a conventional proportional output-type oxygen concentration-sensing device.
Figure 2:
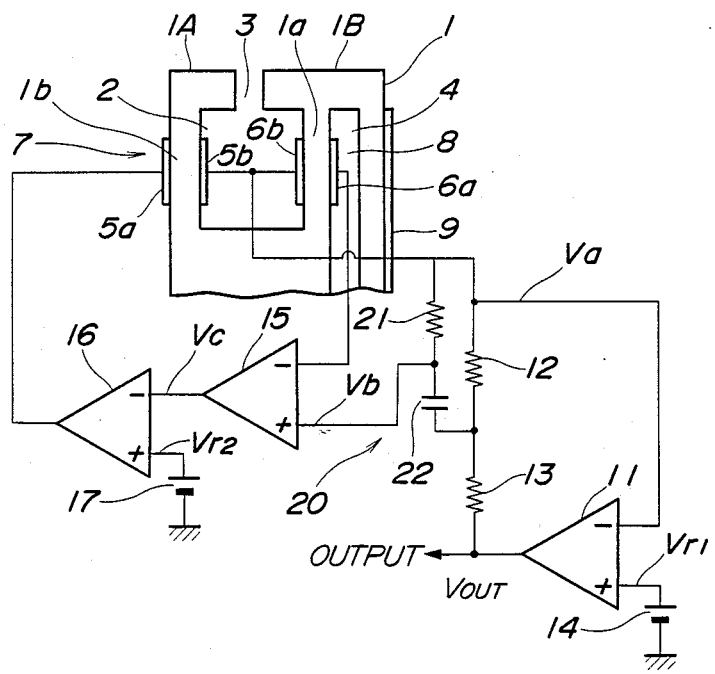
FIG. 2 is a circuit diagram showing an embodiment of the present invention.

Referring first to FIG. 2, there is illustrated an oxygen concentration-sensing device according to the invention, which is adapted for use in an air-fuel ratio feedback control system for an internal combustion engine. The oxygen concentration-sensing device comprises a body 1 formed by a pair of members 1A and 1B, each formed of a solid electrolytic material having oxygen ion-conductivity. The solid electrolytic material may preferably be zirconium dioxide ($ZrO_2$). A gas-staying chamber 2 is defined within the body 1, which serves as a gas diffusion-limiting zone. A gas-introducing slit 3 is formed in the body 1, through which a gaseous substance to be examined, such as exhaust gases from an internal combustion engine, is introduced into the gas-staying chamber 2. The slit 3 is disposed in an exhaust pipe, not shown, of the engine such that exhaust gases in the exhaust pipe can be easily guided into the gas-staying chamber 2 through the slit 3. An air reference chamber 4 which communicates with the atmosphere to be supplied with air is defined within the body 1 at a location adjacent the gas-staying chamber 2 by a wall 1a intervening therebetween and separating them from each other. The wall 1a carries on its opposite sides a couple of electrodes 6a and 6b facing the air reference chamber 4 and the gas-staying chamber 2, respectively. Another wall 1b of the body 1 defining the other side of the gas-staying chamber 2 carries on its opposite sides a couple of electrodes 5a and 5b facing outwardly of the body 1 and the gas-staying chamber 2, respectively. The electrodes 5a, 5b, and 6a, 6b may be formed of platinum (Pt). The member 1A of the body 1 and the electrodes 5a, 5b cooperatively form an oxygen-pumping element 7, while the member 1B and the electrodes 6a, 6b cooperatively form a cell element 8. The body 1 or member 1B has an outer wall defining the air reference chamber 4 and having an outer surface provided with an electrically heating element 9 for heating the oxygen-pumping element 7 and the cell element 8.

The electrode 5b of the oxygen-pumping element 7 and the electrode 6b of the cell element 8 are connected together, and are also connected to an inverting input terminal of an operational amplifier 11. The amplifier 11 has its non-inverting input terminal supplied with a predetermined reference voltage $V_{r1}$ (e.g. 2.5 volts) from a reference voltage source 14. An output voltage $V_{OUT}$ from the operational amplifier 11 represents the sensed oxygen concentration. A series circuit formed of a resistance 12 for phase correction and a resistance 13 for current detection is connected between the inverting input terminal and output terminal of the operational amplifier 11. Connected in parallel with the resistance 12 is another series circuit formed of a resistance 21 and a capacitance 22, the former being connected to the inverting input terminal of the amplifier 11, and the latter being connected to the resistance 13. The resistance value of the resistance 21 is far larger than that of the resistance 12 (e.g. 10 ohms), for example, 100 K ohms. The resistances 12, 13, 21 and capacitance 22 cooperatively form a current-to-voltage converter circuit 20, wherein the junction between the resistance 21 and the capacitance 22 forms a conversion output terminal of the circuit 20, and is connected to the non-inverting input terminal of a differential amplifier 15. The differential amplifier 15 generates an output voltage corresponding to the difference between a potential at the electrode 6a of the cell element 8 and a potential at the conversion output terminal, which output voltage is supplied to another differential amplifier 16. The differential amplifier 16 generates an output voltage corresponding to the difference between the output voltage from the differential amplifier 15 and a predetermined reference voltage $V_{r2}$ from a reference voltage source 17. The predetermined reference voltage $V_{r2}$ from the reference voltage source 17 is set at a value (e.g. 0.45 volts) corresponding to a stoichiometric mixture ratio of a mixture supplied to the engine, at which the maximum conversion efficiency of a three-way catalyst arranged in the engine exhaust pipe can be obtained. The differential amplifier 16 has an output terminal connected to the electrode 5a of the oxygen-pumping element 7.

With the above arrangement, a voltage $V_s$ is developed between the two electrodes 6a, 6b of the cell element 8, which corresponds to the difference in oxygen concentration between the gas-staying chamber 2 and the air reference chamber 4. This voltage $V_s$ is added to a voltage $V_a$ applied to the inverting input terminal of the operational amplifier 11, and the resulting sum is applied to the inverting input terminal of the operational amplifier 11. On the other hand, the voltage $V_a$ applied to the inverting input terminal of the operational amplifier 11 is made almost equal to the output voltage $V_{r1}$ from the reference voltage source 14, applied to the non-inverting input terminal of the amplifier 11, irrespective of whether the pumping current value $I_P$ changes or not, by the action of the amplifier 11. The differential amplifier 15 generates an output voltage $V_c$ corresponding to the difference between the sum $V_s + V_a$ and the voltage $V_b$ at the coversion output terminal, which output voltage is compared with the output voltage $V_{r2}$ from the reference voltage source 17, by the differential amplifier 16.

As the air-fuel ratio of the mixture changes toward the lean side, the voltage $V_s$ between the electrodes 6a, 6b of the cell element 8 decreases. When the voltage $V_c$ corresponding to the difference between the sum $V_s + V_a$ and the voltage $V_b$ drops below the output voltage $V_{r2}$ from the reference voltage source 17 due to the decrease of the voltage $V_s$, the output from the differential amplifier 16 changes into a positive level, which is applied to the electrode 5a of the oxygen-pumping element 7. As a result, pumping current $I_P$ flows through the oxygen-pumping element 7 from the electrode 5a to the electrode 5b and then to the current-to-voltage coverter circuit 20 and the operational amplifier 11. On this occasion, since the pumping current $I_P$ flows from the electrode 5a to the electrode 5b in the oxygen-pumping element 7, oxygen present within the gas-staying chamber 2 is ionized by the electrode 5b, and the resulting ions move through the oxygen-pumping element 7 to be emitted as an oxygen gas from the electrode 5a. Thus, oxygen is pumped out of the gas-staying chamber 2.

As oxygen is thus pumped out of the gas-staying chamber 2, there occurs an increase in the oxygen concentration difference between the gas-staying chamber 2 and the air reference chamber 4. Accordingly, the voltage $V_s$ between the electrodes 6a, 6b of the cell element 8 increases, which is added to the voltage $V_a$, and the resulting increased sum is applied to the inverting input terminal of the differential amplifier 15. The differential amplifier 15 generates an output voltage proportional to the difference between the sum $V_s + V_a$ and the voltage $V_b$, and thus the pumping current $I_P$ is proportional to the oxygen concentration in the exhaust gases.

On the other hand, when the air-fuel ratio has changed toward the rich side, the voltage $V_s$ rises correspondingly. When the output voltage $V_c$ from the differential amplifier 15 correspondingly rises above the output voltage $V_{r2}$ from the reference voltage source 17, the output from the differential amplifier 16 changes into a negative level. This causes reversal of the flow direction of the pumping current $I_P$ flowing between the electrodes 5a, 5b of the oxygen-pumping element 7. That is, the pumping current $I_P$ now flows from the electrode 5b to the electrode 5a so that oxygen outside the body 1 is ionized by the electrode 5a and the resulting ions move through the oxygen-pumping element 7 to be emitted as an oxygen gas into the gas-staying chamber 2. Thus, oxygen is pumped into the gas-staying chamber 2. In this way, the supply of pumping current $I_P$ is controlled so that oxygen is pumped into and out of the gas-staying chamber 2 so as to maintain the oxygen concentration within the gas-staying chamber 2 constant. Therefore, the pumping current $I_P$ varies in proportion to the oxygen concentration in the exhaust gases as the air-fuel ratio of the mixture changes from the lean side to the rich side or vice versa.

The output voltage $V_{OUT}$ from the operational amplifier 11 is expressed by the following equation (1):

$$V_{OUT}=(R_S+R_P)I_P+V_a \quad (1)$$

where $R_S$ represents the resistance value of the resistance 12, and $R_P$ the resistance value of the resistance 13.

The operational amplifier 11 operates such that the input voltage $V_a$ becomes equal to the output voltage $V_{rl}$ from the reference voltage source 14, and hence its output voltage $V_{OUT}$ is proportional to the pumping current $I_P$, i.e. proportional to the oxygen concentration in the exhaust gases.

Figure 3:
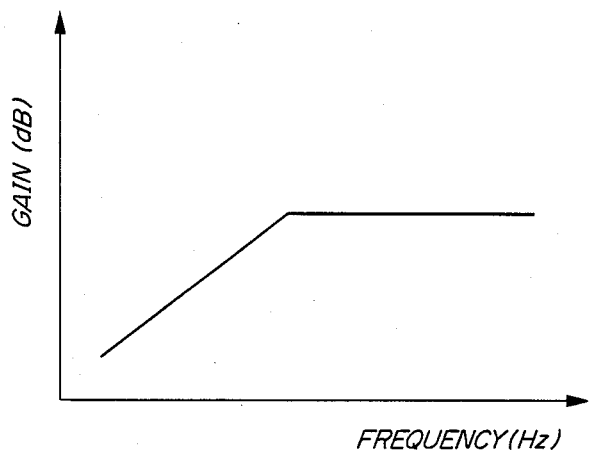
FIG. 3 is a graph showing a conversion output frequency characteristic of a current-to-voltage converter circuit in the device of FIG. 2.
Figure 4:
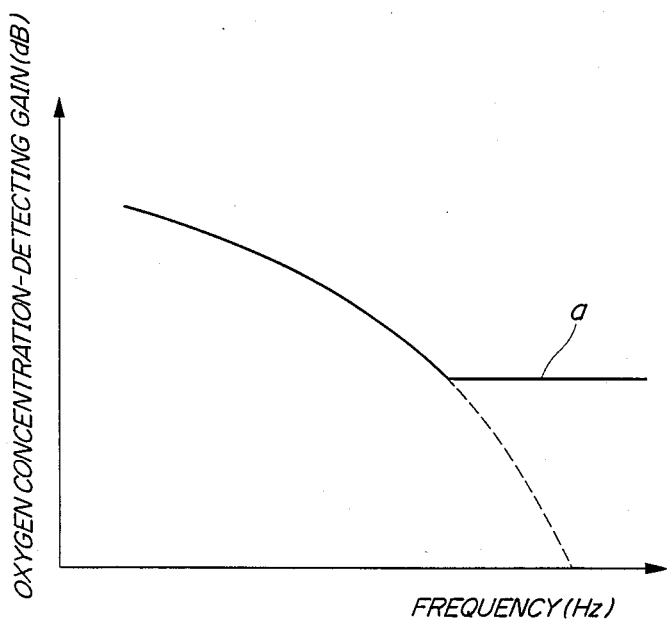
FIG. 4 is a graph showing oxygen concentration-detecting gain vs. frequency in the device of FIG. 2.

In the oxygen concentration-sensing device according to the invention constructed as above, the output voltage at the conversion output terminal of the current-to-voltage converter circuit 20 has a high-pass frequency characteristic as shown in FIG. 3. More specifically, in a high frequency range, the capacitance 22 has reduced AC resistance such that there is a substantial short across the capacitance 22. Since the value of the resistance 21 is far larger than that of the resistance 12, the voltage $V_b$ at the conversion output terminal is nearly equal to the voltage at the junction between the resistances 12, 13. As a result, a sufficient level of detection gain of the oxygen concentration-sensing element is obtained in the high frequency range due to a voltage drop across the resistance 12, as indicated by the solid line a in FIG. 4.

On the other hand, in a low frequency range, the capacitance 22 has increased AC resistance as if the capacitance 22 were not connected between the resistance 21 and the junction between the resistances 12, 13. That is, the voltage $V_b$ at the conversion output terminal is nearly equal to the voltage $V_a$. Therefore, the voltage drop across the resistance 12 so small that it can be disregarded. As a result, the output voltage from the differential amplifier 15 directly corresponds to the voltage $V_s$ across the cell element 8.

By setting the value of the phase correction resistance 12 of the current-to-voltage converter circuit 20 at a sufficiently large value, a sufficient level of detection gain of the oxygen concentration sensing element can be obtained in a high frequency range. This can compensate for phase delay in the high frequency range to thereby prevent oscillation in the same frequency range. On the other hand, in a low frequency range the voltage drop across the phase correction resistance 12 is negligibly small, and hence the pumping current can be controlled to flow in the oxygen-pumping element 7 in direct response to the voltage $V_s$ across the cell element 8, to thereby enable accurate detection of oxygen concentration in a gas to be examined.

What is claimed is:

1. In an oxygen concentration-sensing device including an oxygen concentration-sensing element formed by an oxygen-pumping element and a cell element, each composed of a member of a solid electrolytic material having oxygen ion-conductivity, and a pair of electrodes having said member interposed therebetween, one of said electrodes of said oxygen-pumping element and one of said electrodes of said cell element being connected to each other, said oxygen-pumping element and said cell element defining a gas diffusion-limiting zone therebetween, a current-to-voltage converter circuit having an input terminal connected to a junction between said connected ones of said electrodes, and a conversion output terminal, first amplifier means for generating an output having a level variable in response to a difference between a potential at said conversion output terminal of said current-to-voltage converter circuit and a potential at the other of said electrodes of said cell element, said first amplifier means applying said output thereof to the other of said electrodes of said oxygen-pumping element, and second amplifier means having an input thereof connected to said junction between said connected ones of said electrodes for generating an output proportional to current flowing in said oxygen-pumping element, the improvement wherein said current-to-voltage converter circuit includes gain-changing means for imparting a higher gain to said first amplifier means when said current flowing in said oxygen-pumping element is in a high frequency range.

2. An oxygen concentration-sensing device as claimed in claim 1, wherein said gain-changing means of said current-to-voltage converter circuit comprises means for making said potential at said conversion output terminal closer or equal to a potential at said junction between said connected ones of said electrodes when said current flowing in said oxygen-pumping element is in said high frequency range.

3. An oxygen concentration-sensing device as claimed in claim 1 or claim 2, wherein said second amplifier means has an output terminal and an inverting input terminal, and said current-to-voltage converter circuit comprises a resistance connected between said junction between said connected ones of said electrodes and said conversion output terminal, a voltage-dividing circuit having a divided voltage output terminal and connected between said output terminal and said inverting input terminal of said second amplifier means, and a capacitive impedance element connected between said divided voltage output terminal of said voltage-dividing circuit and said conversion output terminal.

4. In an oxygen concentration-sensing device including an oxygen concentration-sensing element formed by an oxygen-pumping element and a cell element, each composed of a member of a solid electrolytic material having oxygen ion-conductivity, and a pair of electrodes having said member interposed therebetween, said oxygen-pumping element and said cell element defining a gas diffusion-limiting zone therebetween, one of said electrodes of said oxygen-pumping element and one of said electrodes of said cell element being connected to each other, a current-to-voltage converter circuit having an input terminal connected to a junction between said connected ones of said electrodes, and a conversion output terminal, differential amplifier means for generating an output voltage corresponding to a difference between a potential at said conversion output terminal of said current-to-voltage converter circuit and a potential at the other of said electrodes of said cell element, voltage-applying means for applying to the other of said electrodes of said oxygen-pumping element a voltage corresponding to a difference between said output voltage from said differential amplifier means and a predetermined reference voltage, and operational amplifier means having a non-inverting input terminal supplied with a predetermined reference voltage, an inverting input terminal connected to said junction between said connected ones of said electrodes, and an output terminal, said current-to-voltage converter circuit being connected between said inverting input terminal and said output terminal, the improvement wherein said current-to-voltage converter circuit comprises a resistance connected between said junction between said connected ones of said electrodes and said conversion output terminal, a voltage-dividing circuit having a divided voltage output terminal and connected between said output terminal and said inverting input terminal of said operational amplifier means, and a capacitive impedance element connected between said divided voltage output terminal of said voltage-dividing circuit and said conversion output terminal.

* * * * *